(12) United States Patent
Whitham

(10) Patent No.: US 6,445,766 B1
(45) Date of Patent: Sep. 3, 2002

(54) SYSTEM AND METHOD FOR IMPROVED DIAGNOSTIC IMAGING IN A RADIATION TREATMENT SYSTEM

(75) Inventor: Kenneth Whitham, Alamo, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/693,702

(22) Filed: Oct. 18, 2000

(51) Int. Cl.[7] .................................................. A61N 5/10
(52) U.S. Cl. .......................................... 378/65; 378/124
(58) Field of Search ........................... 378/65, 124, 125, 378/126

(56) References Cited

U.S. PATENT DOCUMENTS 5,046,078 A  *  9/1991  Hernandez et al. ......... 378/119
5,471,516 A  *  11/1995  Nunan ......................... 378/65
5,757,881 A  *  5/1998  Hughes ....................... 378/65

* cited by examiner

*Primary Examiner*—Robert H. Kim
*Assistant Examiner*—Hoon K. Song

(57) ABSTRACT

A radiation therapy system according to the present invention includes a treatment system and an imaging system. The treatment system employs a first tungsten target to generate high power X-rays for treatment. The imaging system uses a second target to generate low power X-rays for imaging. The targets are arranged such that the resulting treatment and imaging beams are generally collinear.

12 Claims, 3 Drawing Sheets

SYSTEM AND METHOD FOR IMPROVED DIAGNOSTIC IMAGING IN A RADIATION TREATMENT SYSTEM

BACKGROUND OF THE INVENTION

1. Field of the Invention

The present invention relates to X-ray diagnostic imaging and, in particular, to X-ray diagnostic imaging in a radiation therapy treatment system.

2. Description of the Related Art

The use of linear accelerators in medicine is well known. Such linear accelerators are used for treating patients with radiation therapy, such as X-rays or electron beams. Such X-rays are created when high energy electrons are decelerated in a target material such as tungsten.

In such radiation therapy systems, it is desirable to obtain X-ray images for treatment diagnosis and treatment planning. Typically, radiation therapy systems use full energy electron beams to produce X-rays for diagnostic imaging. These high energy X-rays (about 2 MeV) produce washed out images that are difficult to interpret.

An alternative is to use low voltage sources, but typical low voltage sources are not collinear with the treatment beam. Consequently, the accuracy of the subsequent therapy relies on interpreting the relative position of the two beams.

As such, there is a need for a radiation therapy device that employs low power X-rays for imaging that are substantially aligned with treatment X-rays.

SUMMARY OF THE INVENTION

These and other drawbacks in the prior art are overcome in large part by a system and method according to the present invention. A diagnostic target is provided substantially adjacent a treatment target at an X-ray exit window or aperture in a linear accelerator. In a normal or treatment mode, a guide or bending magnet directs an electron beam toward the treatment target, generating X-rays directed at the patient. In a diagnostic mode, the guide magnet is turned off and the electron beam is directed at the diagnostic target such that diagnostic X-rays are directed at the patient. High energy X-rays are absorbed by head shielding. Low energy (about 500 keV) X-rays are used for diagnostic imaging. The high energy treatment beam and the low energy imaging beam are substantially collinear, thereby allowing use of the same beam shielding device hardware in both modes.

A radiation therapy system according to the present invention includes a treatment system and an imaging system. The treatment system employs a first tungsten target to generate high power X-rays for treatment. The imaging system uses a second target to generate low power X-rays for imaging. The targets are arranged such that the resulting treatment and imaging beams are collinear.

BRIEF DESCRIPTION OF THE DRAWINGS

A better understanding of the invention is obtained when the following detailed description is considered in conjunction with the following drawings in which.

DETAILED DESCRIPTION OF THE INVENTION

FIG. 1–4 illustrate an improved radiation therapy system with diagnostic imaging according to an implementation of the invention. A diagnostic target is provided substantially adjacent a treatment target at an X-ray exit window or aperture in a linear accelerator. In a normal or treatment mode, a guide magnet directs an electron beam toward the treatment target, generating X-rays directed at the patient. If electron beam treatment is desired, no treatment target is used in treatment mode. In a diagnostic mode, the guide magnet is turned off and the electron beam is directed at the diagnostic target such that diagnostic X-rays are directed at the patient. High energy X-rays are absorbed by head shielding. Low energy (about 500 keV) X-rays are used for diagnostic imaging. The high energy treatment beam and the low energy imaging beam are substantially collinear, thereby allowing use of the same beam shielding device hardware in both modes.

Figure 1:
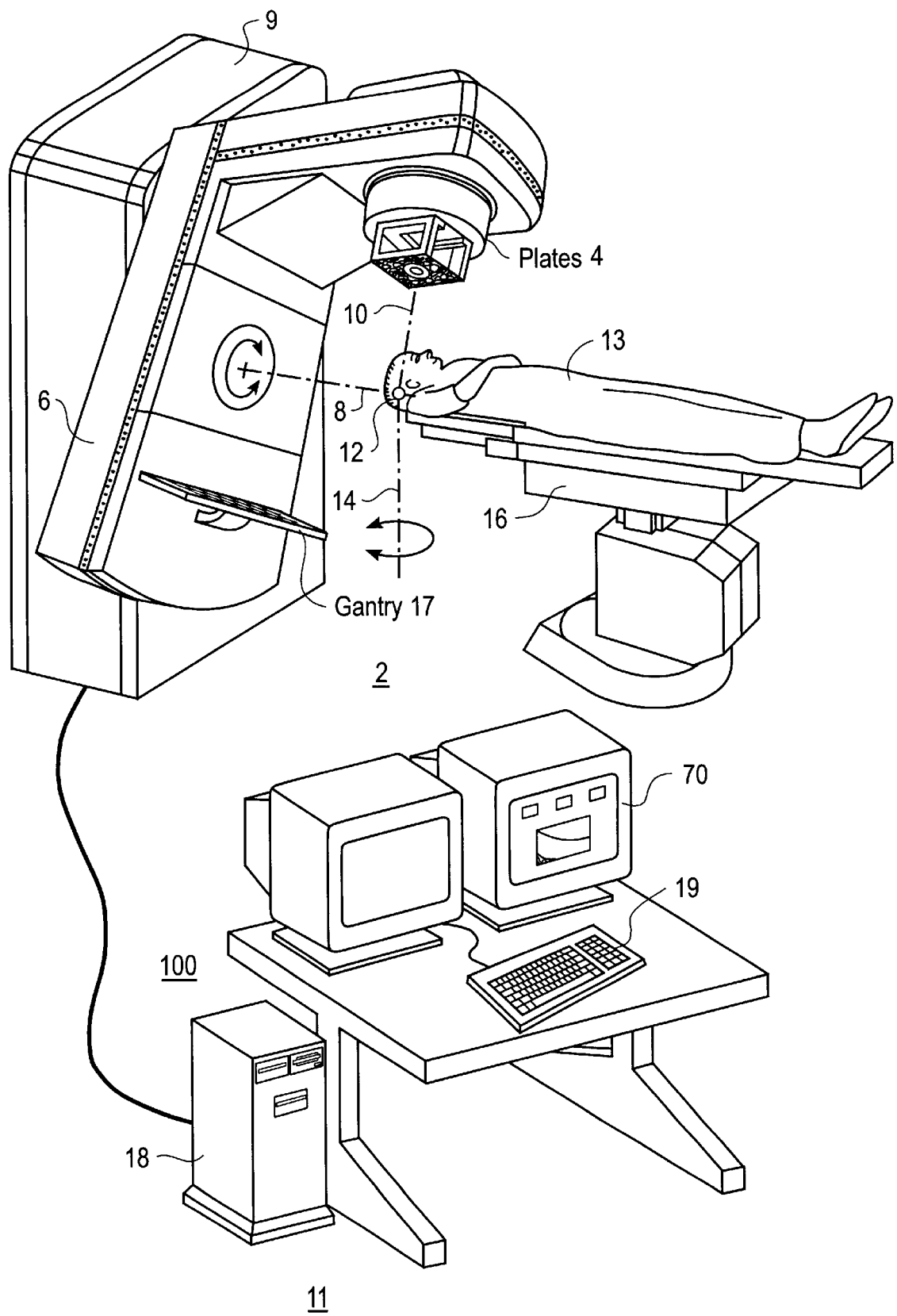
FIG. 1 is a diagram of a prior art radiation therapy system suitable for use with with a system in accordance with an implementation of the invention.

FIG. 1 illustrates a radiation emitting system 11. The radiation emitting system 11 includes a radiation treatment device 2 of common design, which utilizes plates 4 and a control unit in a housing 9 along with a treatment processing unit 100 constructed in accordance with the present invention. The radiation treatment device 2 includes a gantry 6 which can be swiveled around a horizontal axis of rotation 8 in the course of therapeutic treatment. Plates 4 are fastened to a projection of gantry 6. To generate the high-powered radiation required for the therapy, a linear accelerator is located in gantry 6. The axis of the radiation bundle emitted from the linear accelerator and gantry 6 is designated 10. Electron, photon, or any other detectable radiation can be used for the therapy.

During the treatment, the radiation beam is trained on a zone 12 of an object 13, for example, a patient who is to be treated, and who lies at the isocenter of the gantry rotation. The rotational axis 8 of the gantry 6, the rotational axis 14 of a treatment table 16, and the beam axis 10 all preferably intersect in the isocenter. In addition, an imaging unit 17 may be provided for diagnostic or setup purposes. The construction of such a radiation treatment device is described in general in a brochure "Digital Systems for Radiation Oncology", Siemens Medical Laboratories, Inc. A91004-M2630-B358-01 -4A00, September 1991. An exemplary radiation treatment system is the Primus system, available from Siemens Medical Systems, Inc., Concord, Calif. The imaging unit may be the Beamview system, also available from Siemens Medical Systems, Inc., Concord, Calif.

Figure 2:
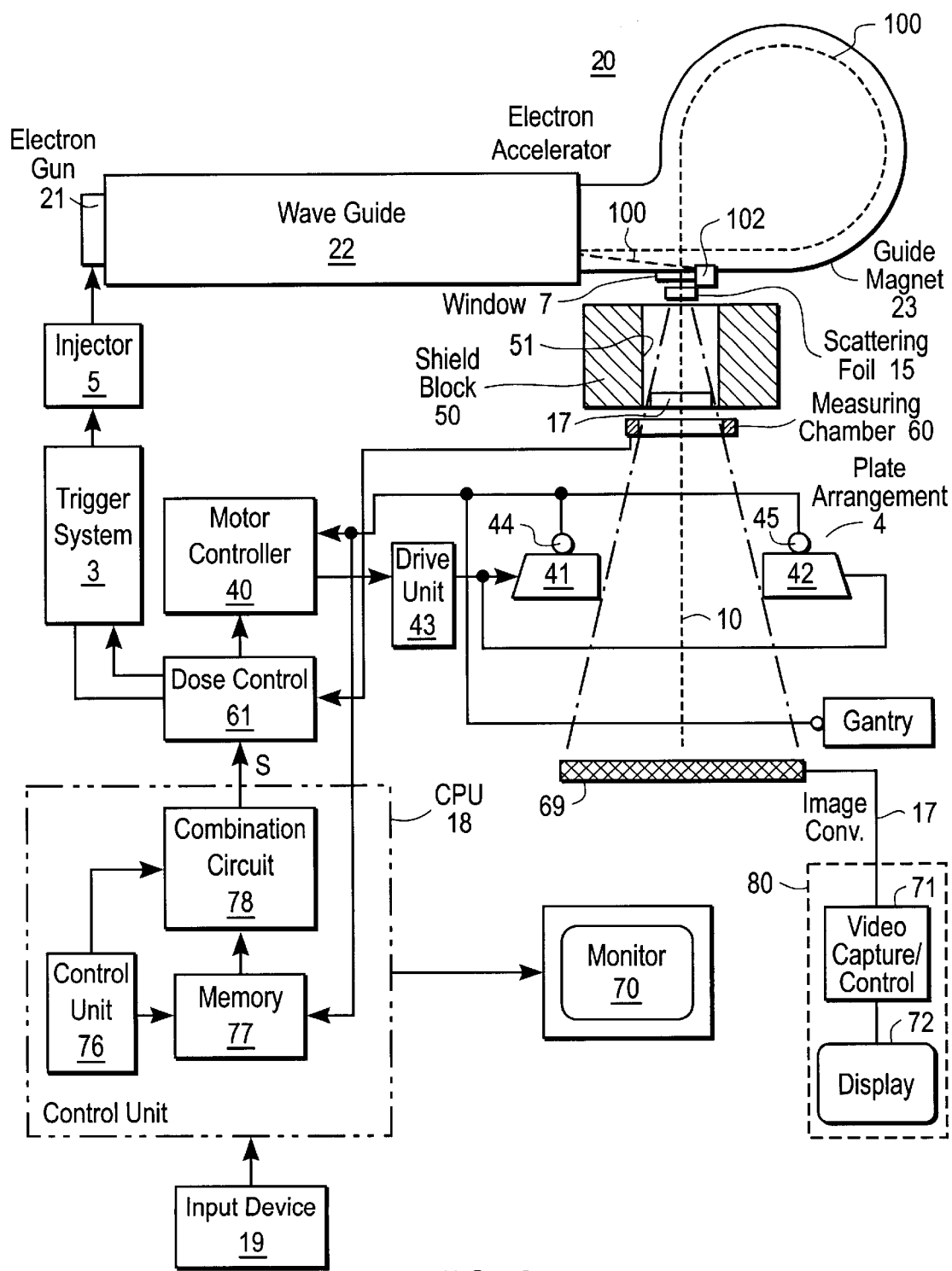
FIG. 2 is a block diagram of a radiation therapy system in accordance with an embodiment of the present invention.

FIG. 2 shows a portion of an illustrative radiation treatment device 2 and portions of treatment processing unit 100 in more detail. An electron beam 1 is generated in an electron accelerator 20. The accelerator 20 includes an electron gun 21, a wave guide 22, and an evacuated envelope or guide magnet housing 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, the beam is sent through a measuring chamber 60, in which the dose is ascertained. If the scattering foils are replaced by a target, the radiation beam is an X-ray beam. Finally, aperture plate arrangement 4 includes a pair of plates 41 and 42. Of course, this is just one example of a beam-shielding arrangement that can be used in the invention. The invention is suitable in other arrangements, as is well appreciated by those skilled in the art. For example, the beam shielding arrangement may be a multi-leaf collimator employing a plurality of thin leaves.

Plate arrangement or beam shielding device 4 may be embodied as one or more pairs of aperture plates 41 and 42 and additional pairs of aperture plates (not shown) arranged perpendicular to plates 41 and 42. in order to change the size of the irradiated field, the aperture plates can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions. The plate arrangement 4 is employed both in the treatment mode and in the imaging mode, as will be explained in greater detail below.

The area of a patient that is irradiated is known as the field. As is well known, plates 4 are substantially impervious to the emitted radiation. They are mounted between the radiation source and patient in order to delimit the field. Areas of the body, for example, healthy tissue, are therefore subjected to as little radiation as possible, and preferably to none at all. Preferably, with at least one of the plate movable, the distribution of radiation over the field need not be uniform (one region can be given a higher dose than another); further, with the gantry able to be rotated, different beam angles and radiation distributions are allowed without having to move the patient around.

The central treatment processing or control unit 100 (FIG. 1) is usually located apart from radiation treatment device 2 in a different room to protect the therapist from radiation. Treatment processing unit 100 includes an output device, such as at least one visual display unit or monitor 70, and an input device, such as a keyboard 19, although data can be input also through data carriers, such as data storage devices. The treatment processing unit 100 is typically operated by the therapist who administers actual delivery of a radiation treatment as prescribed by an oncologist. By utilizing keyboard 19, or other input device, the therapist enters into a control unit 76 of the treatment processing unit 100 the data that defines the radiation to be delivered to the patient, for example, according to the prescription of the oncologist. The program can also be input via another input device, such as a data storage device, through data transmission. On the screen of a monitor 70, various data can be displayed before and during the treatment.

Central processing unit 18 (FIG. 2), included in treatment processing unit 100, is connected with the input device, e.g., keyboard 19, for inputting the prescribed delivery of the radiation treatment and with a dose control unit 61 that generates the desired values of radiation for the controlling trigger system 3. Trigger system 3 suitably adapts the pulse repetition frequency or other parameters to change the radiation output. A digital dosimetry system is particularly advantageous in order to more easily control the digital output of central processing unit 18. Central processing unit 18 suitably includes a control unit 76 for controlling execution of the treatment program in conjunction with memory 77 and a combination circuit 78 which suitably receives signals from the control unit 76 and memory 77 for combination to produce a set signal, S, that identifies a dose rate for dose rate control unit 61 in accordance with the present invention.

In addition, as will be explained in greater detail below, the CPU 18 generates control signals to turn off the guide magnet and redirect the electron beam using in-plane steering coils (not shown) through a diagnostic target 102 for diagnostic imaging using the imaging unit 17.

More particularly, an imaging unit 17 is provided such that an image detector 69 is positioned in opposition to the treatment head and the diagnostic target 102. The image detector is coupled to an imaging station 80, which includes a video control unit 71 for capturing video images and controlling imaging operation, and a display 72 for displaying the resulting images. In one implementation, the video control unit 71 is implemented as a video camera, video capture board, and various processing circuitry. In this implementation, the image detector 69 is a metal foil scintillation detector. Alternatively, the image detector 69 may be implemented as a flat panel detector comprising one or more arrays of photosensitive cells.

Figure 3:
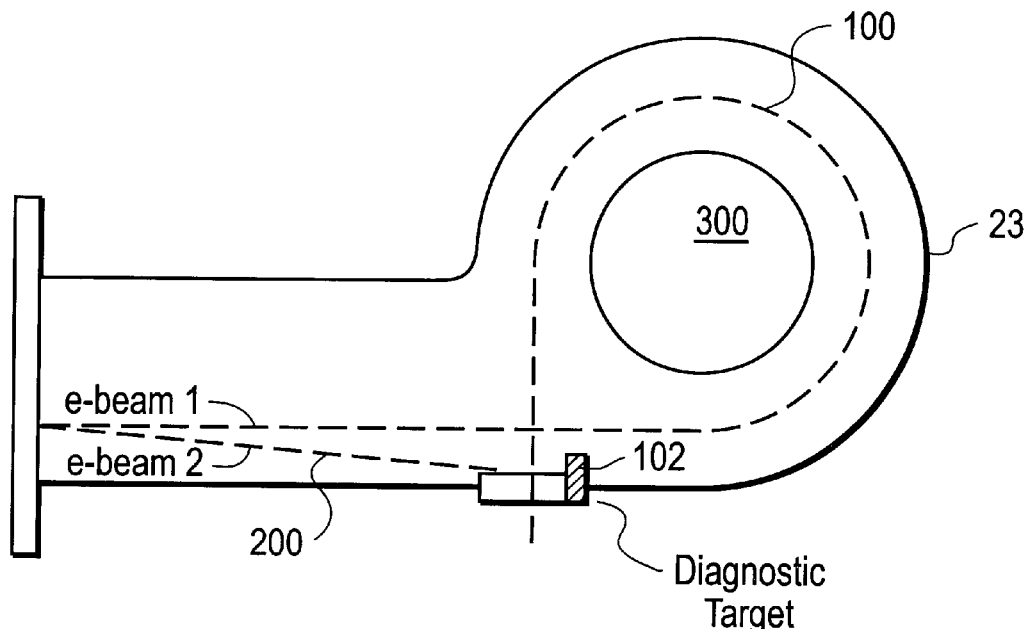
FIG. 3 is a diagram illustrating beam direction according to an implementation of the invention.

The use of the diagnostic target is illustrated in greater detail with reference to FIG. 3. As shown, the guide magnet housing 23 includes the guide magnet 300, and the diagnostic target 102. In a first mode, the CPU 18 supplies control signals to cause the guide magnet 300 to be activated and the X-ray beam 100 to be generated, as described above. In a diagnostic mode, the CPU 18 generates control signals to turn off the guide magnet 300 and engage in-plane steering coils (not shown) the steer the beam 200 into the diagnostic target 102. Forward or high energy X-rays area absorbed by the head shielding. Ninety degree, 500 keV X-rays are used to obtain clearer pictures.

Figure 4:
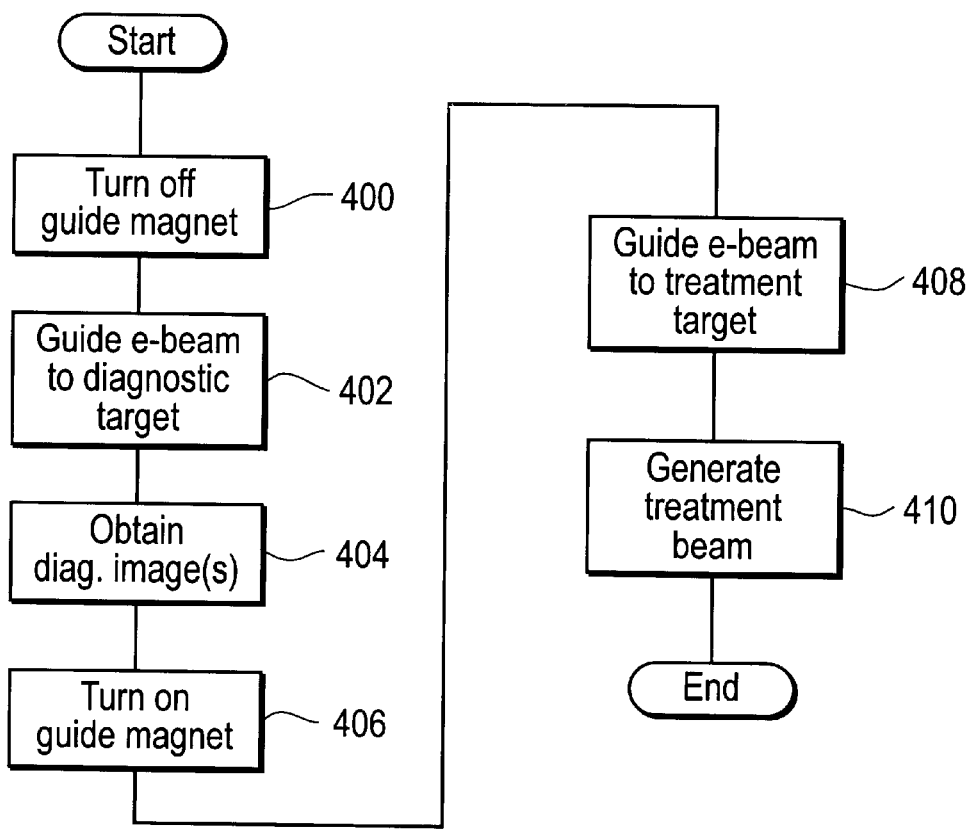
FIG. 4 is a flowchart illustrating a method according to an implementation of the invention.

Turning now to FIG. 4, a flowchart illustrating operation of an implementation of the invention is shown. In a step 400, the CPU 18 sends control signals to turn off the guide magnet 300. In a step 402, the in-plane steering coils are used to guide the electron beam 200 to the diagnostic target. The diagnostic target, which may be formed of copper or tungsten, for example, is positioned such that low energy 90 degree X-rays are provided for imaging. In a step 404, the resulting 90 degree X-rays are used to obtain one or more images. Once the desired images have been obtained, the CPU sends control signals to turn on the guide magnet 300, in a step 406. In a step 408, the electron beam 100 is guided to impinge on a treatment target (if desired) and the treatment beam is generated in step 410.

The invention described in the above detailed description is not intended to be limited to the specific form set forth herein, but is intended to cover such alternatives, modifications and equivalents as can reasonably be included within the spirit and scope of the appended claims.

What is claimed is:

1. A radiation therapy device operable in a first mode and a second mode, comprising:
   a control unit for controlling application of radiation in said first mode and said second mode; and
   an electron accelerator, said electron accelerator including:

an electron gun;

a waveguide for receiving an electron beam from said electron gun;

a guide magnet for directing said electron beam to a desired target via a window in said first mode; and a diagnostic target, wherein said electron beam is directed at said diagnostic target in said second mode.

2. A radiation therapy device in accordance with claim 1, said electron beam adapted to undergo 90 degree Compton scattering in said diagnostic target.

3. A radiation therapy device in accordance with claim 2, further including an imaging unit adapted to receive resulting scattered radiation for diagnostic imaging.

4. A radiation therapy device operable in a first mode and a second mode, comprising:

a control unit for controlling application of radiation in said first mode and said second mode; and an electron accelerator, said electron accelerator including:

an electron gun;

a waveguide for receiving an electron beam from said electron gun;

a guide magnet housing having a guide magnet for directing said electron beam to a desired target via a window in said guide magnet housing in said first mode; and a diagnostic target, positioned substantially adjacent said window, wherein said electron beam is directed at said diagnostic target in said second mode.

5. A radiation therapy device in accordance with claim 4, said electron beam adapted to undergo 90 degree Compton scattering in said diagnostic target.

6. A radiation therapy device in accordance with claim 5, further including an imaging unit adapted to receive resulting scattered radiation for diagnostic imaging.

7. A radiation therapy device comprising:

a radiation beam source;

an imaging unit employing a first target for generating low energy imaging beams from said radiation beam source;

a treatment unit employing a second target for generating high energy treatment beams from said radiation beam source;

wherein said first target and said second target are positioned substantially adjacent one another such that a resulting treatment beam and a resulting imaging beam are substantially collinear.

8. A radiation therapy device according to claim 7:

said imaging unit and said treatment unit adapted to employ a same beam shielding device for imaging and treatment.

9. A radiation therapy method, comprising:

providing a radiation beam source providing a radiation therapy unit having a first target for generating treatment beams from said radiation beam source;

providing an imaging unit having a second target for generating imaging beams from said radiation beam source;

wherein said first target and said second target are positioned such that resulting treatment and imaging beams are substantially collinear.

10. A method according to claim 9, further comprising providing one or more plate arrangements suitable for use for imaging and treatment.

11. A radiation treatment method, comprising:

generating low power X-rays using a first target, said low power X-rays being used for diagnostic imaging;

generating high power X-rays using a second target, said high power X-rays being used for treatment, wherein said low power X-rays and said high power X-rays are generated generally collinearly and wherein said generating said high power X-rays comprises activating a guide magnet and directing an electron beam at said second target;

said generating low power X-rays comprising deactivating said guide magnet and directing said electron beam at said first target.

12. An electron accelerator, comprising:

an electron gun;

a waveguide for receiving an electron beam from said electron gun;

a guide magnet for directing said electron beam to a desired target via a window in a first mode; and a diagnostic target, wherein said electron beam is directed at said diagnostic target in a second mode, said electron beam in said first mode and said second mode being generally collinear.

* * * * *